(12) United States Patent
Abdel-Monem et al.

(10) Patent No.: US 7,129,375 B2
(45) Date of Patent: Oct. 31, 2006

(54) METAL COMPLEXES OF α AMINO DICARBOXYLIC ACIDS

(75) Inventors: Mahmoud M. Abdel-Monem, Moscow, ID (US); Michael D. Anderson, Eden Prairie, MN (US)

(73) Assignee: Zinpro Corporation, Eden Prairie, MN (US)

( * ) Notice: Subject to any disclaimer, the term of this patent is extended or adjusted under 35 U.S.C. 154(b) by 505 days.

(21) Appl. No.: 10/272,382

(22) Filed: Oct. 16, 2002

(65) Prior Publication Data

US 2004/0077714 A1    Apr. 22, 2004

(51) Int. Cl.
    C07C 229/00    (2006.01)
(52) U.S. Cl. ..................... 562/571; 562/573
(58) Field of Classification Search ............... 562/553, 562/561, 563, 565, 571, 573; 514/492, 494, 514/499, 501
    See application file for complete search history.

(56) References Cited

U.S. PATENT DOCUMENTS

| | | | |
|---|---|---|---|
| 2,810,754 A | 10/1957 | Chang |
| 2,849,468 A | 8/1958 | Cardinal |
| 2,915,540 A | 12/1959 | Chang |
| 3,084,189 A | 4/1963 | Chang |
| 3,168,541 A | 2/1965 | Hobbs |
| 3,174,986 A | 3/1965 | Motozaki |
| 3,463,858 A | 8/1969 | Anderson |
| 3,911,117 A | 10/1975 | Ender |
| 3,925,433 A | 12/1975 | Abdel-Monem |
| 3,941,818 A | 3/1976 | Abdel-Monem |
| 3,950,372 A | 4/1976 | Abdel-Monem |
| 4,021,569 A | 5/1977 | Abdel-Monem |
| 4,039,681 A | 8/1977 | Abdel-Monem |
| 4,067,994 A | 1/1978 | Anderson |
| 4,145,465 A | 3/1979 | Sanderson et al. |
| 4,167,564 A | 9/1979 | Jensen |
| 4,216,143 A | 8/1980 | Ashmead |
| 4,216,144 A | 8/1980 | Ashmead |
| 4,228,090 A | 10/1980 | Hydes |
| 4,425,280 A | 1/1984 | Ho |
| 4,460,734 A | 7/1984 | Owens et al. |
| 4,517,330 A | 5/1985 | Zdanowski et al. |
| 4,599,152 A | 7/1986 | Ashmead |
| 4,670,269 A | 6/1987 | Abdel-Monem |
| 4,678,854 A | 7/1987 | Abdel-Monem |
| 4,764,633 A | 8/1988 | Anderson |
| 4,824,661 A * | 4/1989 | Wagner ................. 424/52 |
| 4,830,716 A | 5/1989 | Ashmead |
| 4,900,561 A | 2/1990 | Abdel-Monem |
| 4,948,594 A | 8/1990 | Abdel-Monem |
| 4,956,188 A | 9/1990 | Anderson |
| 5,061,815 A | 10/1991 | Leu |
| 5,200,198 A | 4/1993 | Geisslinger et al. |
| 5,278,329 A | 1/1994 | Anderson |
| 5,348,749 A | 9/1994 | Sikter |
| 5,401,770 A | 3/1995 | Taguchi et al. |
| 5,409,905 A | 4/1995 | Eby, III |
| 5,430,164 A | 7/1995 | Abdel-Monem |
| 5,504,055 A | 4/1996 | Hsu |
| 5,505,968 A | 4/1996 | Schaefer et al. |
| 5,516,925 A | 5/1996 | Pedersen et al. |
| 5,569,458 A | 10/1996 | Greenberg |
| 5,583,243 A | 12/1996 | Abdel-Monem |
| 5,698,724 A | 12/1997 | Anderson |
| 5,728,675 A | 3/1998 | Schaefer et al. |
| 5,885,610 A | 3/1999 | Anderson |
| 6,126,928 A | 10/2000 | Swaile |
| 6,166,071 A | 12/2000 | Ashmead et al. |
| 6,169,118 B1 | 1/2001 | Bilali |
| 6,210,690 B1 | 4/2001 | Nabeshima et al. |
| 6,218,192 B1 | 4/2001 | Altura et al. |
| 6,242,009 B1 | 6/2001 | Batarseh et al. |
| 6,248,368 B1 | 6/2001 | Valletta |
| 6,323,354 B1 | 11/2001 | Moore |

FOREIGN PATENT DOCUMENTS

EP    0 514 553 A1    11/1992
WO    PCT/US03/26672    1/2004

OTHER PUBLICATIONS

Gramaccioli, Acta Cryst. (1996) 21, 600.*
Gramaccioli, Acta Cryst. (1966) 21, 594.*

* cited by examiner

*Primary Examiner*—Thurman K. Page
*Assistant Examiner*—Karl Puttlitz
(74) *Attorney, Agent, or Firm*—McKee, Voorhees & Sease, P.L.C.

(57) ABSTRACT

Neutral alpha amino diacid complexes of trace minerals and their use for animal nutrition.

4 Claims, No Drawings

METAL COMPLEXES OF α AMINO DICARBOXYLIC ACIDS

FIELD OF THE INVENTION

This invention relates to the field of animal feed supplements and more particularly to the preparation and nutritional value of novel metal complexes of α-amino-dicarboxylic acids such as aspartic and glutamic acids.

BACKGROUND OF THE INVENTION

The presence of essential metals in sufficient quantities and in a biologically available form in diet is essential for maintaining the health and well being of domestic animals and poultry. Because essential metals such as copper, iron, manganese and zinc are often deficient in common feed ingredients, supplemental amounts of these nutrients are often added to the feed of domesticated animals and poultry. Many commercial feed additives have been developed to provide the essential metals in forms that are readily biologically utilizable. The degree of biological availability of nutrients is often referred to as "bioavailability". Bioavailability of essential metals depends on the physical and/or chemical properties of the form in which the metal is present in the diet. Increased bioavailability of supplemental metals is beneficial because it allows the use of lower concentrations of the metals in the diet to meet the nutritional needs of animals, while lowering the potential harmful effects of high levels of these metals both on the animals and on the environment.

Several commercial products are available in which trace elements are more bioavailable than the corresponding inorganic source of the metal. The enhanced bioavailability is attributed to the association of the metal with an organic molecule, generally known as ligand. This association or bonding results in the increased availability of the metal for utilization by animals, i.e. increased bioavailability. The increased bioavailability of the essential elements in these products is the result of increased solubility, greater stability in the gut, enhanced absorption into circulation and/or improved metabolic utilization.

Different types of products that contain a trace element associated with an organic ligand are commercially available. These can be classified in different groups based on the nature of the ligand used in manufacturing the product. In one class of products, amino acids are used as the ligands that form complexes or chelates with the metal. Examples of these products are described in U.S. Pat. Nos. 3,941,818; 3,950,372; 4,067,994; 4,863,898 4,900,561; 4,948,594; 4,956,188; 5,061,815; 5,278,329; 5,583,243; and 6,166,071. A second group of feed additives include the metal salts of short chain carboxylic acids such as propionic acid (See U.S. Pat. Nos. 5,591,878, 5,707,679, 5,795,615 and 5,846,581). A third group of trace element additives is classified by the American Feed Control Officials as Metal Proteinate and defined as "the product resulting from the chelation of a soluble salt with amino acids and/or partially hydrolyzed protein". Examples of these products are described in U.S. Pat. Nos. 3,440,054, 3,463,858, 3,775,132, 3,969,540, 4,020,158, 4,076,803, 4,103,003, 4,172,072 and 5,698,724.

The common assignee of the present application has in the past synthesized and patented metal complexes of amino acids as a more bioavailable source of the essential elements. The following are examples of these patents: U.S. Pat. Nos. 3,941,818; 3,950,372; 4,021,569; 4,039,681; and 4,067,994 disclose 1:1 complexes of alpha amino acids, preferably DL-methionine with the transition metals zinc, chromium, manganese and iron. The formation of similar complexes with L-methionine is disclosed in U.S. Pat. No. 5,278,329. U.S. Pat. Nos. 4,900,561 and 4,948,594 disclose copper complexes of alpha amino acids containing terminal amino groups. Complexes of copper, manganese, zinc and iron with alpha hydroxyl aliphatic carboxylic acids are disclosed in U.S. Pat. Nos. 4,956,188 and 5,583,243. U.S. Pat. Nos. 4,670,269 and 4,678,854 disclose complexes of cobalt with poly-hydroxyl carboxylic acid such as glucoheptanoic acid. Complexes of the amino acid L-lysine with trace elements are disclosed in U.S. Pat. No. 5,061,815. The effectiveness of the compounds disclosed in these patents has been demonstrated from data provided in some of these patents and in numerous scientific publications and technical reports.

The above patents describe the use of pure synthetic or natural amino or hydroxyl acids. In U.S. Pat. No. 5,698,724 the assignee of the current application disclosed the synthesis of complexes of essential elements with natural amino acids obtained by the hydrolysis of proteins. Since this patent was issued, a large number of field studies have demonstrated that metals from these complexes are more bioavailable than metals from inorganic sources.

Based on our experience with metal-amino acid complexes as described in the references cited above, we have concluded that the 1:1 complexes of the metals Zn, Mn, Cu, Co, Fe are effective nutritional sources of the metals and more advantageous than the 1:2 complexes. These 1:1 complexes exist as ion pairs in which the metal-amino acid comprises the cation. The counter ion (anion) is provided by a mineral acid and is necessary for balancing the charge on the cation. The requirement for the external anion results in products in which the metal content is limited. The purpose of the present invention is to develop metal amino acid complexes in which the amino acid serves a dual role. It serves as the bidentate ligand to form a complex with the metal ion, and the counter ion to balance the charge on the cationic complex. This allows the preparation of stable crystalline complexes that contain 20–30% metal. The alpha amino dicarboxylic acids aspartic and glutamic acids are examples of suitable ligands that meet these requirements.

A careful review of the patent and scientific literature indicated that some sources make reference to compounds containing metals and aspartic or glutamic acid. However, it is not always clear what complexes are being described and what is the relevance of this prior art to the intended use of these complexes in nutrition contemplated in the present invention. Two scientific reports were published in 1966 describing the crystal structures of copper glutamate dihydrate and zinc glutamate dihydrate. In the first report copper glutamate dihydrate was obtained by the slow evaporation of a solution of glutamic acid and copper nitrate (The Crystal Structure of Copper Glutamate Dihydrate, Carlo M. Gramaccioli and Richard E. Marsh, Acta Cryst., 21, 594 (1966)) The structure of the blue-green crystals was determined by x-ray crystallography. A companion paper reported the structure of the zinc glutamate dihydrate crystals obtained by the evaporation of an aqueous solution of zinc oxide in glutamic acid (The Crystal Structure of Zinc Glutamate Dihydrate, Carlo M. Gramaccioli, Acta Cryst., 21, 600 (1966)).

Several salts of aspartic acid and glutamic acid with alkali metals such as sodium, potassium, calcium and magnesium are commercially available. Magnesium aspartate containing 17–20% magnesium and calcium aspartate containing 20% calcium are commercially available and are likely the neutral salts containing one magnesium or calcium cation neutralized by one dibasic anion of aspartic acid. Calcium and zinc acid salts of aspartic and glutamic acids that contain one dibasic cation and two molecules of the dibasic acids are commercially available.

Magnesium aspartate is included among organic salts of magnesium used for the treatment or prophylaxis of auto immune diseases in the text and claims of U.S. Pat. No. 6,248,368 B1. However, magnesium pyrophosphate is singled out as the preferred magnesium salt according to this invention. A method and composition for treatment of headache using magnesium salts are described in U.S. Pat. No. 6,218,192 B1. Although magnesium aspartate and magnesium aspartate hydrochloride appeared among magnesium salts mentioned in the text, the focus appeared to be the administration of water soluble magnesium salts, specifically magnesium sulfate and magnesium chloride. U.S. Pat. No. 6,210,690 B1 describes a water-in-oil type emulsified composition for use in skin and hair cosmetics. These emulsions are stabilized by different additives including salts of amino acids. Although magnesium aspartate and magnesium and calcium glutamates were included among the possible amino acid salts listed in the text, only sodium glutamate was listed in the claims. A flavor blend for masking the unpleasant taste of zinc compounds is disclosed in U.S. Pat. No. 6,169,118 B1. In the text of this patent the inventors mention zinc aspartate as one of the examples of zinc compounds that may benefit from the teachings of the invention.

The texts of two related patents teach that magnesium aspartate hydrochloride may be used as one of the electrolytes in an antemortem nutrient supplement for livestock (U.S. Pat. Nos. 5,505,968 and 5,728,675). U.S. Pat. No. 5,401,770 describes zinc complexes of natural alpha-amino acids as antipruritic agents. In these complexes the molar ratio of the amino acid to zinc is 2:1. A microbicidal composition obtained by combining under acidic conditions of equimolar amounts of a metal salt, an amino acid and an inorganic acid is described in U.S. Pat. No. 6,242,009 B1. Among the metal salts listed are those of silver, zinc, copper, mercury, chromium, manganese, nickel, cadmium, arsenic, cobalt, aluminum, lead, selenium, platinum, gold, titanium, tin or their combinations. As well, glutamic and aspartic acids are among amino acids listed. A cure for common cold containing a highly ionizable zinc compound is described in U.S. Pat. No. 5,409,905. The inventor states that zinc complexes such as zinc citrate, zinc aspartate and zinc amino acid chelates are too tightly bound at pH 7.4 to release sufficient zinc ions to be useful and are outside the scope of the invention.

A number of U.S. patents make reference to metal salts of glutamic and aspartic acids in conjunction with other inventions. U.S. Pat. No. 2,810,754 describes the use of the copper glutamate complex as an intermediate in the preparation of glutamine from glutamic acid. The recovery of glutamic acid from solutions containing it by precipitation of zinc glutamate salts is described in U.S. Pat. No. 2,849,468. U.S. Pat. No. 4,167,564 describes a method for improving the stability of amino acid-metal complexes containing 2–16 moles of the amino acid per one mole of metal by incorporating in the mixture a buffer system that controls the pH of the complex and its surrounding media. Amino acid chelates consisting of a metal ion chelated to one or more ligands and are essentially free of anion radicals other than hydroxyl and anions of weak organic acids are described in U.S. Pat. No. 4,599,152. A method for the production of ferrous monoglutamate by reacting in aqueous solution a ferrous salt with a glutamic acid material is described in U.S. Pat. No. 3,168,541. An improved diet for fur-bearing animals such as mink is described in U.S. Pat. No. 3,911,117. The diet contains raw marine fish and a chelate of ferric iron with an organic acid. However, the exact chemical nature of the ferric ion chelate with the organic acids is not described.

Two related U.S. patents describe a hair treatment composition to improve the delivery of amino acids to the hair and scalp by forming a "particulate metal-amino acid complex" the metals described in the patent included zinc (U.S. Pat. No. 5,911,978 and U.S. Pat. No. 6,228,353). The text and claims of these patents list 9 amino acids including glutamic acid. However, the examples in both patents use cystine, a sulfur amino acid that contains two carboxyl and two alpha amino groups. The zinc complex formed with cystine is vastly different than that formed between zinc and glutamic acid. U.S. Pat. No. 5,348,749 describes the use of metal-amino acid complexes among other substances for the treatment of panic disorders. Zinc salts of glutamic and aspartic acids containing two molecules of the amino acid per one zinc ion are among the compounds described in this patent.

None of the above described references, have any specific description of neutral complexes of dicarboxylic acids, such as aspartic and glutamic in which the amino acid serves a dual role as the bidentate ligand that forms a complex with the trace mineral metal ion and as the counter ion to balance the charge of the cationic complex. It is, therefore, a primary object of this invention to provide such neutral complexes in a stable form that provide 20%–30% by weight metal.

Another object is to provide nutritional supplements for animal/poultry feed that contain these neutral complexes.

Yet another objective is to provide a method of nutritional supplementation of animals and poultry that provides bio-available trace minerals, and amino acids without any significant pollution risk.

And, a yet further object is to provide an efficient and economical process of making the complexes of this invention.

The method and manner of accomplishing these and other objectives will become apparent from the written description which follows.

SUMMARY OF THE INVENTION

This invention relates to the development of novel metal amino acid complexes that are more effective in meeting the dietary needs of animals and humans than currently available metal sources. The metals are more bioavailable from these complexes than the inorganic forms. These complexes have commercial potential because they are stable and can be obtained by practical methods at a reasonable cost without risk of environmental pollution.

Compounds described in this invention are neutral complexes of one of the essential trace elements such as copper, manganese and zinc with di-carboxylic α-amino acids such as glutamic acid and aspartic acid. The amino acid ligand is selected to serve a dual role, as the bidentate ligand that forms a complex with the metal ion, and as the counter ion to balance the charge on the cationic complex of the metal and amino-carboxyl moiety.

DETAILED DESCRIPTION OF A PREFERRED EMBODIMENT

It is now well established that essential metals are more bioavailable from amino acid complexes than from inorganic forms of the metal. The majority of the essential metal-amino acid complexes can be classified under one of two major groups based on the ratio of the metal to amino acid in the complex. The first group is the complexes in which the ratio of essential metal to amino acid is 1:1. These complexes usually exist as ion pairs in which the cation is composed of the metal amino acid complex and the anion is that of a mineral acid such as sulfuric or hydrochloric acid. These complexes are usually readily soluble in water and have high bioavailability. One draw back of these complexes is that they are hygroscopic. The complexes in the carrier-free dry form are difficult to handle and absorb moisture during shipping, storage and blending with other feed ingredients. Therefore, these complexes are usually available blended with suitable carriers to improve their physical properties. This results in a product that has limited metal content often in the 10–15% range. The second group of metal amino acid complexes is that in which the ratio of the metal to amino acid is 1:2. Complexes in this group usually are sparingly soluble in water. They often are present as stable powders with good physical properties for blending with other feed ingredients. Some of the shortcomings of this group include cost, i.e. they contain relatively high fraction of their weight in the form of the usually expensive amino acids. Another shortcoming is that the metal content is low and is limited by the molecular weight of the amino acid. A third and more significant shortcoming is that for these complexes to serve as a source of the bioavailable metal, they must dissolve in the acid contents of the gastrointestinal tract. Under the acidic conditions at the absorption site the complexes re-equilibrate in solution to provide the 1:1 complexes and free amino acids. As such, the 1:2 metal-amino acid complexes are serving as costly and usually less effective pro-nutrients for the 1:1 complexes.

In the present invention, we describe novel metal-amino acid complexes that retain the favorable characteristics of the previously known 1:1 and 1:2 complexes and are devoid of their shortcomings. These novel complexes are more effective in meeting the dietary needs of animals and humans than currently available metal sources. The essential metals are more bioavailable from these complexes than from the inorganic sources and other organic trace metal complexes currently available. These complexes have commercial potential because they are stable and can be obtained by practical methods at a reasonable cost.

The neutral complexes of this invention are neutral complexes of one of the essential trace elements with di-carboxylic α-amino acids. The amino acid ligand is selected to serve a dual role, as the bidentate ligand that forms a 1:1 complex with the metal ion, and as the counter ion to balance the charge on the cationic complex of the metal and amino-carboxyl moiety. Like the currently known and popular 1:1 complexes, the novel complexes are fed as the 1:1 complexes which are the predominant species in the pH at the absorption site in the gastrointestinal tract of animals. But unlike the other 1:1 complexes, the novel complexes have excellent physical properties so they can be shipped, stored and added to feed in the carrier-free form that has a relatively high metal content. When compared to the 1:2 complexes, the novel complexes share their excellent physical properties. However, the novel complexes have the advantage of being fed in the form that will be predominant at the pH of the absorption site without the need for an additional amino acid molecule that will not participate in the uptake of the metal. Therefore, the novel complexes can be obtained with higher metal content than the corresponding 1:2 complexes.

In summary, the novel complexes described in this invention have the following advantages over currently available metal-amino acid complexes:
1) The essential trace elements are more bioavailable from the novel complexes.
2) The metal content of the complexes is higher.
3) The novel complexes have excellent physical properties that make manufacturing, shipping, storing and blending into feed easier.
4) The novel complexes are more stable.
5) The novel complexes can be obtained by practical methods at a lower cost.

Suitable trace metals are: zinc, copper, manganese, iron, cobalt, nickel, vanadium and molybdenum. Preferred elements are: zinc, copper, and manganese.

The useful amino dicarboxylic acids are: aspartic, glutamic, 1,6-Dicarboxylic-2-amino hexanoic, 1,7-dicarboxylic-2-amino heptanoic and 1,8-dicarboxylic-2-amino octanoic acid. Preferred acids are aspartic and glutamic acids.

The products may be used in the carrier-free form or with a carrier. Suitable carriers include: calcium hydrogen phosphate, calcium carbonate, silica, ground corn cobs, and powdered sugar or a mixture of any of the above.

The metal amino acid complexes described in this invention may be obtained by a variety of methods. Most of these methods involve the reaction of the amino acid directly with a metal oxide or indirectly by first forming the di-sodium salt followed by reaction with a metal salt. The use of L-glutamic acid or L-Aspartic acid has several disadvantages including relatively high cost, relatively low availability and low water solubility.

The preparation of the metal complexes from the reaction of the amino acids with metal oxide was attempted. Because of the low solubility of the amino acids, a suspension of the acid in water was mixed with the water insoluble metal oxide to give the metal complexes that have low water solubility. This resulted in a contaminated product that required extensive crystallization. This approach was abandoned as being of low practical value. Alternatively, the amino acid was dissolved in a solution of sodium hydroxide (or other base such as potassium hydroxide) to form the di-sodium salt of the amino acid. The solution was then treated with either the metal oxide or a solution of the metal salt to give the metal-amino acid complex. This approach provided products of inconsistent quality. When the metal oxide was used, the quality of the product was inconsistent and contained variable amounts of contamination with un-reacted metal oxide. When a solution of the metal salt was used, the reaction conditions had to be carefully controlled to avoid the precipitation of the metal hydroxides.

A practical process was developed for the preparation of the metal amino acid complexes on a large scale at a reasonable cost. This process involves the mixing of a solution of the readily water soluble monosodium glutamate with a solution of a water soluble metal salt. The pH of this solution is adjusted by the careful addition of a solution of a molar equivalent of a base. This results in the formation of crystals of the metal-amino acid complex. The physical nature of the crystals can be controlled by two factors, the concentration of reactant in the reaction mixture and the rate of cooling of the reaction mixture after the addition of the base. When the concentration of reactants was high or when the reaction mixture was cooled quickly, small crystals were formed. Adjusting the pH to neutral should be done with slow addition with stirring to avoid formulation of high pH spikes which endures formation of insoluble metal hydroxides. Quick cooling can be done by use of an ice water bath to cool down to 20° C., usually in one-half hour or less, depending upon batch size. When the concentration of reactants was low or when the reaction mixture was cooled slowly, large crystals were formed. The advantages of this process include:

1) Monosodium glutamate is readily commercially available at a reasonable cost. Its cost is significantly lower than that of L-glutamic acid. L-glutamic acid is nearly 2.5 times as expensive as monosodium glutamate;
2) Monosodium glutamate is readily soluble in water and its solution is slightly acidic. Mixing a solution of monosodium glutamate with a solution of a metal salt does not result in the formation of insoluble metal hydroxides;
3) The overall cost of production is lower because only one-half the amount of a base is required for the final pH adjustment and formation of the desired product; and
4) The product obtained by this process is consistently of higher quality than those obtained by using L-glutamic acid as a starting material.

In summary, the practical and economical process described in this invention for preparing the novel metal amino acid complexes has several advantages including:

a) Lower cost, the complexes can be obtained at a lower cost because of the lower cost of the primary ingredient (amino acid) and smaller quantity of base used;
b) Higher product yield. Usually 90–95% of the product crystallizes out of solution. Further concentration of the supernatant provides additional crystals. Alternatively, the supernatant is used as the solvent in the preparation of other batches of product;
c) Better product quality. The fact that both the amino acid and the metal can be mixed in solution at a neutral to slightly acidic pH prevents the formation of insoluble metal hydroxides; and
d) Greater consistency. The reaction conditions can be easily controlled which results in a more consistent product and a simpler process.

The following examples are offered to illustrate the practical methods of obtaining these complexes, their physical and chemical properties, and their use as a source of trace elements in animal nutrition.

EXAMPLE 1

Preparation of Zinc Glutamate Dihydrate from Glutamic Acid

Glutamic Acid (148.65 g, 1.0 mole) was added to a solution of sodium hydroxide (81.07 g, 2.0 moles) in 500 ml of distilled water. The mixture was heated with vigorous stirring until all solids dissolved. To this clear solution was added slowly a solution of zinc chloride (149.936 g, 1.1 moles) with continued heating and stirring. A crystalline precipitate began to form. The heating was stopped and the stirring was continued until the mixture reached room temperature. The mixture was stored at 5° C. for 18 hours. The crystals were filtered and washed with two 100 ml portions of cold water. The precipitate was dried at 75–80° C. for 8 hours.

|  | Found | Theory* | Yield |
|---|---|---|---|
| Weight of product | 249 g | 246.55 g | 101.00% |
| Zinc (EDTA Titration) | 26.68% | 26.52% | 100.61% |

*Calculated for Zinc Glutamate Dihydrate

FTIR in a Potassium Bromide Pellet: Absorption peaks @ about 3309.6 (m), 3255.6 (m), 3178.5 (w), 2962.5 (w), 1620.1 (vs), 1566.1 (vs), 1415.7 (s), 1334.6 (s), 1284.5 (m), 1114.8 (m), and 609.5 (m) cm$^{-1}$. (w, weak; m, medium; s, strong; and vs, very strong).

EXAMPLE 2

Preparation of Zinc Glutamate Dihydrate from Monosodium Glutamate

Monosodium Glutamate Monohydrate (748.545 g, 4.0 moles) was added to 700 ml of distilled water and the mixture was heated with vigorous stirring until all solids dissolved. To this clear solution was added slowly a solution of zinc chloride (556.257 g, 4.0 moles) with continued heating and stirring. A cooled solution of sodium hydroxide (162.105 g, 4.0 moles) in 400 ml of distilled water was added slowly with continued stirring. A crystalline precipitate began to form. The heating was stopped and the mixture was placed in an ice-water bath. Stirring was continued until the mixture reached room temperature. The mixture was stored at 5° C. for 18 hours. The crystals were filtered and washed with two 100 ml portions of cold water. The precipitate was dried at 75–80° C. for 8 hours.

|  | Found | Theory* | Yield |
|---|---|---|---|
| Weight of product | 946 g | 986.20 g | 95.93% |
| Zinc (EDTA Titration) | 26.71% | 26.52% | 100.72% |
| Glutamic Acid (Ninhydrin Assay) | 58.28% | 60.30% | 96.65% |

*Calculated for Zinc Glutamate Dihydrate

FTIR in a Potassium Bromide Pellet: Absorption peaks @ about 3328.9(m), 3253.7(m), 2923.9(w), 1616.2 (vs), 1562.2 (vs), 1409.9 (s), 1330.8(m), 1271.0(m), 1103.2(m), and 572.8 (m) cm$^{-1}$. (w, weak; m, medium; s, strong; and vs, very strong).

EXAMPLE 3

Preparation of Copper Glutamate Dihydrate from Glutamic Acid

Glutamic Acid (148.641 g, 1.0 mole) was added to a solution of sodium hydroxide (81.079 g, 2.0 moles) in 500 ml of distilled water. The mixture was heated with vigorous stirring until all solids dissolved. To this clear solution was added slowly a solution of copper chloride (170.498 g, 1.0 mole) with continued heating and stirring. A crystalline precipitate began to form. The heating was stopped and the stirring was continued until the mixture reached room temperature. The mixture was stored at 5° C. for 24 hours. The crystals were filtered and washed with two 50 ml portions of cold water. The precipitate was dried at 75–80° C. for 8 hours.

|  | Found | Theory* | Yield |
|---|---|---|---|
| Weight of product | 247 g | 244.676 g | 100.94% |
| Copper (Iodine Titration) | 25.34% | 25.97% | 97.58% |

*Calculated for Copper Glutamate Dihydrate

FTIR in a Potassium Bromide Pellet: Absorption peaks @ about 3317.3 (m), 3224.8 (m), 2931.6 (w), 1627.8 (vs), 1573.8 (vs), 1407.9 (s), 1353.9 (w), 1326.9 (w), 1265.2 (m), 1134.1 (m), and 759.9 (m) cm$^{-1}$. (w, weak; m, medium; s, strong; and vs, very strong).

EXAMPLE 4

Preparation of Copper Glutamate Dihydrate from Monosodium Glutamate

Monosodium Glutamate Monohydrate (187.140 g, 1.0 mole) was added to 200 ml of distilled water and the mixture was heated with vigorous stirring until all solids dissolved. To this clear solution was added slowly a solution of copper chloride dihydrate (172.283 g, 1.0 mole) in 200 ml of water with continued heating and stirring. A cooled solution of sodium hydroxide (40.509 g, 1.0 mole) in 100 ml of distilled water was added slowly with continued stirring. The mixture was placed in an ice-water bath and stirring was continued. A blue crystalline precipitate began to form. The mixture was stored at 5° C. for 18 hours. The crystals were filtered and washed with two 50 ml portions of cold water. The precipitate was dried at 75–80° C. for 8 hours.

|  | Found | Theory* | Yield |
|---|---|---|---|
| Weight of product | 234 g | 244.706 g | 95.63% |
| Copper (Iodine Titration) | 26.50% | 25.97% | 102.04% |

*Calculated for Copper Glutamate Dihydrate

FTIR in a Potassium Bromide Pellet: Absorption peaks @ about 3313.5(s), 3219.0 (s), 1625.9 (vs), 1573.8 (vs), 1456.2 (w), 1406.0 (s), 1394.4 (s), 1355.9(m), 1267.1(m), 1132.1 (m), and 758.0 (m) cm$^{-1}$. (w, weak; m, medium; s, strong; and vs, very strong).

EXAMPLE 5

Preparation of Copper Glutamate Dihydrate from Monosodium Glutamate

Monosodium Glutamate Monohydrate (748.522 g, 4.0 moles) was added to 700 ml of distilled water and the mixture was heated with vigorous stirring until all solids dissolved. To this clear solution was added slowly a solution of copper sulfate pentahydrate (1019.135 g, 4.0 moles) in 900 ml of water with continued heating and stirring. A cooled solution of sodium hydroxide (162.101 g, 4.0 moles) in 400 ml of distilled water was added slowly with continued stirring. A vigorous reaction occurred and a green crystalline precipitate began to form. The mixture was placed in an ice-water bath and stirring was continued. The mixture was stored at 5° C. for 18 hours. The crystals were filtered and the precipitate was dried at 75–80° C. for 8 hours.

|  | Found | Theory* | Yield |
|---|---|---|---|
| Weight of product | 992 g | 978.82 g | 101.35% |
| Copper (Iodine Titration) | 25.45% | 25.97% | 98.00% |

*Calculated for Copper Glutamate Dihydrate

The product was divided into two portions and each was mixed with 400 ml of water. The mixture was heated with stirring and then filtered. The precipitate was washed with two 100 ml portions of water. The precipitate was dried at 75–80° C. for 8 hours.

|  | Found | Theory* | Yield |
|---|---|---|---|
| Weight of product | 922 g | 978.82 g | 94.20% |
| Copper (Iodine Titration) | 27.29% | 25.97% | 105.09% |

*Calculated for Copper Glutamate Dihydrate

The product appears to be a mixture the copper glutamate dihydrate and anhydrous copper glutamate. The recovery of copper in the purification step is 99.67%.

FTIR in a Potassium Bromide Pellet: Absorption peaks @ about 3313.5(s), 3228.6 (s), 1629.7 (vs), 1573.8 (vs), 1456.2 (w), 1406.0 (s), 1388.7 (s), 1263.3 (m), 1132.1(m), and 758.0 (m) cm$^{-1}$. (w, weak; m, medium; s, strong; and vs, very strong).

EXAMPLE 6

Preparation of Manganese Glutamate Dihydrate from Glutamic Acid

Glutamic Acid (148.672 g, 1.0 mole) was added to a solution of sodium hydroxide (81.049 g, 2.0 moles) in 500 ml of distilled water. The mixture was heated with vigorous stirring until all solids dissolved. To this clear solution was added slowly a solution of manganese chloride tetrahydrate (197.932 g, 1.0 mole) in 300 ml of water with continued heating and stirring. A crystalline precipitate began to form after few minutes. The heating was stopped and the stirring was continued until the mixture reached room temperature. The mixture was stored at 5° C. for 24 hours. The crystals were filtered and washed with two 50 ml portions of cold water. The precipitate was dried at 75–80° C. for 8 hours.

|  | Found | Theory* | Yield |
|---|---|---|---|
| Weight of product | 221 g | 236.098 g | 93.61% |
| Manganese (EDTA Titration) | 23.52% | 23.27% | 101.08% |

*Calculated for Manganese Glutamate Dihydrate

FTIR in a Potassium Bromide Pellet: Absorption peaks @ about 3332.8 (m), 3251.8 (m), 2912.3 (w), 1608.5 (vs), 1546.8 (vs), 1419.5 (s), 1361.7 (w), 1330.8 (w), 1276.8 (w), 1087.8 (s), and 783.0 (m) cm$^{-1}$. (w, weak; m, medium; s, strong; and vs, very strong).

EXAMPLE 7

Preparation of Manganese Glutamate Dihydrate from Monosodium Glutamate

Monosodium Glutamate Monohydrate (748.536 g, 4.0 moles) was added to 700 ml of distilled water and the mixture was heated with vigorous stirring until all solids dissolved. To this clear solution was added slowly a solution of manganese chloride tetrahydrate (807.815 g, 4.0 moles) in 700 ml of water with continued heating and stirring. A cooled solution of sodium hydroxide (162.082 g, 4.0 moles) in 400 ml of distilled water was added slowly with continued stirring. A voluminous light brown crystalline precipitate began to form. The mixture was placed in an ice-water bath and stirring was continued. The mixture was stored at 5° C. for 18 hours. The crystals were filtered and the precipitate was dried at 75–80° C. for 8 hours.

|  | Found | Theory* | Yield |
|---|---|---|---|
| Weight of product | 886 g | 944.39 g | 93.82% |
| Manganese (EDTA Titration) | 23.42% | 23.27% | 100.65% |

*Calculated for Manganese Glutamate Dihydrate

The product was divided into two portions and each was mixed with 400 ml of water. The mixture was heated with stirring and then filtered. The precipitate was washed with two 100 ml portions of water. The precipitate was dried at 75–80° C. for 8 hours.

|  | Found | Theory* | Yield |
|---|---|---|---|
| Weight of product | 852 g | 944.39 g | 90.22% |
| Manganese (EDTA Titration) | 23.97% | 23.27% | 103.01% |

*Calculated for Manganese Glutamate Dihydrate

The product appears to be a mixture the manganese glutamate dihydrate and anhydrous manganese glutamate. The recovery of manganese in the purification step is 98.43%.

FTIR in a Potassium Bromide Pellet: Absorption peaks @ about 3338.6(s), 3244.0 (s), 2906.5 (m), 1604.7 (vs), 1544.9 (vs), 1440.7 (s), 1326.9 (s), 1274.9 (s), 1085.8(s), 765.7 (s) and 559.3 (s) (m) cm$^{-1}$. (w, weak; m, medium; s, strong; and vs, very strong).

EXAMPLE 8

Preparation of Zinc Aspartate from Aspartic Acid

Aspartic Acid (135.825 g, 1.0 mole) was added to a solution of sodium hydroxide (81.043 g, 2.0 moles) in 300 ml of distilled water. The mixture was heated with vigorous stirring until all solids dissolved. To this clear solution was added slowly a solution of zinc chloride (152.967 g, 1.1 moles) in 200 ml of water with continued heating and stirring. A crystalline precipitate began to form. The heating was stopped and the stirring was continued until the mixture reached room temperature. The mixture was stored at 5° C. for 18 hours. The crystals were filtered and washed with two 100 ml portions of cold water. The precipitate was dried at 75–80° C. for 8 hours.

|  | Found | Theory* | Yield |
|---|---|---|---|
| Weight of product | 49.468 g | 196.38 g | 25.19% |
| Zinc (EDTA Titration) | 37.04% | 33.29% | 111.27% |

*Calculated for Anhydrous Zinc Aspartate

FTIR in a Potassium Bromide Pellet: Absorption peaks @ about 3423.4 (m), 3257.5 (m), 2929.7 (w), 1602.7 (vs), 1577.7 (vs), 1438.8 (s), 1396.4 (m), 1224.7 (w), 1184.2 (m), and 690.5 (w) cm$^{-1}$. (w, weak; m, medium; s, strong; and vs, very strong). The filtrate from above was allowed to evaporate slowly to give several crops of crystals of product.

EXAMPLE 9

Comparison of Various Sources of Zinc on Feed Intake, Average Daily Gain and Feed Efficiency in Male Broilers Male commercial broilers were used in the study. The trial started on day 4 posthatching and ended on day 18. Two hundred eighty eight (288) were used in a completely randomized design of 8 treatments in 6 replications of 6 broilers each. The treatments were Basal Diet, Basal Diet+ 15 ppm zinc from zinc sulfate, Basal Diet+30 ppm zinc from zinc sulfate, Basal Diet+45 ppm zinc from zinc sulfate, Basal Diet+15 ppm zinc from zinc aspartate, Basal Diet+30 ppm zinc from zinc aspartate, Basal Diet+15 ppm zinc from zinc glutamate, Basal Diet+30 ppm zinc from zinc glutamate. The Basal Diet did not contain a zinc source additive but was found by analysis to contain 42.73 ppm zinc. Zinc sulfate, zinc aspartate and zinc glutamate were added as a 1% premix into the dietary treatments.

Feed intake and average daily weight gain were determined for each treatment. The growth performance was analyzed as a completely randomized design. Pen of broilers (6 broilers each) served as the experimental unit. Linear and quadratic contrasts statements appropriate for equally spaced treatments were used to determine differences in treatment means. Multiple linear regressions using the slope-ratio test were used to compare efficacies of tested products and calculate the bioavailability of zinc aspartate and zinc glutamate relative to zinc sulfate (RBV). The calculated relative bioavailabilities of zinc aspartate and zinc glutamate are summarized in Table 1.

TABLE 1

Relative Bioavailability of Zinc Aspartate and Zinc Glutamate in Broilers

| Parameter | Relative Bioavailability (RBV, %) |
|---|---|
| Average Daily Weight Gain |  |
| Zinc Aspartate | 121.76 |
| Zinc Glutamate | 169.54 |
| Average Daily Feed Intake |  |
| Zinc Aspartate | 108.89 |
| Zinc Glutamate | 190.65 |

From the above data, it can be seen that the invention accomplishes its enumerated objectives. The data evidences the stability of the complexes, the desirability of ease of processability compared to hygroscopic 1:1 complexes, and their efficiency when fed to boiler chicks.

The complexes described in this invention are more effective in meeting the dietary needs of animals and humans than currently available metal sources. This is attributed to higher bioavailability of the metal from these complexes. A demonstration of the higher bioavailability of the zinc complexes relative to zinc sulfate in male broilers is shown in "Example 9". Other studies provided similar responses confirming the practical utility of this invention. Table 2 lists the recommended feeding amounts of these complexes in different animal species. It should be emphasized that these feeding amounts are based on general industry standards and may be modified to meet the special needs of animals in question, diet composition and concentrations of the metal from other sources in the diet.

TABLE 2

| | Recommended Feeding Amounts | | | | | | | | |
|---|---|---|---|---|---|---|---|---|---|
| | Cattle | | | Swine | | | Chicken | | |
| Compound | Calves | Feedlot | Dairy | Starter | G-F | Breeding | Layers | Broilers | Turkeys |
| | g/head/day | | | ppm | | | | | |
| Zinc Glutamate | 1.357 | 1.357 | 1.357 | 151 | 75 | 151 | 151 | 151 | 151 |
| Manganese Glutamate | 0.859 | | 0.859 | 43 | 86 | 86 | 172 | 172 | 172 |
| Copper Glutamate | 0.481 | 481 | 0.481 | 193 | | 96 | | | |

As a general guideline beyond Table 2 for zinc, manganese and copper glutamates, the general range of feeding amounts should be within these guidelines:

1) Zinc glutamate may be fed at the rate of 110–1100 ppm of zinc glutamate equivalent to 30–300 ppm zinc depending on the animal species. Preferred level is 50–300 ppm of zinc glutamate.
2) Manganese glutamate may be fed at the rate of 20–770 ppm of manganese glutamate equivalent to 5–180 ppm manganese depending on the animal species. Preferred level is 40–210 ppm of manganese glutamate.
3) Copper glutamate may be fed at the rate of 20–190 ppm of copper glutamate equivalent to 5–50 ppm copper depending on the animal species. Preferred level is 40–110 ppm of copper glutamate.

It goes without saying that changes and modifications of structure and formulation may be made to the compounds and nutritional formulations, especially those which preserve the basic neutral complex and dual dicarboxylic acid role, and still come within the scope, spirit and claims of the invention.

What is claimed is:

1. A 1:1 neutral complex of an essential trace element and a dicarboxylic alpha amino-acid, wherein said neutral complex is combined with a suitable animal feed carrier selected from the group consisting of calcium hydrogen phosphate, calcium carbonate, silica, ground corn cobs, and powdered sugar or a mixture of any of the above.

2. A 1:1 neutral complex of a trace element selected from the group consisting of: zinc, copper and manganese and an alpha amino acid selected from aspartic acid, wherein said neutral complex is combined with a suitable animal feed carrier selected from the group consisting of calcium hydrogen phosphate, calcium carbonate, silica, ground corn cobs, and powdered sugar or a mixture of any of the above.

3. A 1:1 neutral complex of a trace element selected from the group consisting of: zinc, copper and manganese and an alpha amino acid selected from glutamic acid, wherein said neutral complex is combined with a suitable animal feed carrier selected from the group consisting of calcium hydrogen phosphate, calcium carbonate, silica, ground corn cobs, and powdered sugar or a mixture of any of the above.

4. A nutritional supplement composition for animals comprising an animal feed carrier and a nutritionally supplementing affective amount of a 1:1 neutral complex of an essential trace element and a dicarboxylic alpha amino acid.

* * * * *